United States Patent [19]

Schmitt et al.

[11] 4,224,172

[45] Sep. 23, 1980

[54] OIL-SOLUBLE ADDUCTS OF BENZOTRIAZOLE AND OXAZOLINES AND LUBRICANT COMPOSITIONS CONTAINING SAME

[75] Inventors: Kirk D. Schmitt; Robert F. Bridger, both of Hopewell, N.J.

[73] Assignee: Mobil Oil Corporation, New York, N.Y.

[21] Appl. No.: 965,819

[22] Filed: Dec. 4, 1978

Related U.S. Application Data

[63] Continuation of Ser. No. 785,813, Apr. 8, 1977, abandoned.

[51] Int. Cl.$^2$ .............................................. C10M 1/32
[52] U.S. Cl. ................................. 252/51.5 R; 548/239
[58] Field of Search ............... 252/51.5 R; 260/308 B, 260/307 F; 548/239

[56] References Cited

U.S. PATENT DOCUMENTS

| | | | |
|---|---|---|---|
| 3,377,239 | 4/1968 | Holan | 260/307 F X |
| 3,399,209 | 8/1968 | Holan et al. | 260/307 F |
| 3,448,115 | 6/1969 | Holan et al. | 260/307 F X |
| 3,472,863 | 10/1969 | Holan et al. | 260/307 F X |
| 3,785,982 | 1/1974 | Okoroduou | 252/515 R X |
| 3,914,179 | 10/1975 | Byford et al. | 252/56 S X |
| 4,049,564 | 9/1977 | Ryer et al. | 252/51.5 R X |

*Primary Examiner*—Andrew Metz
*Attorney, Agent, or Firm*—Charles A. Huggett; Raymond W. Barclay; Howard M. Flournoy

[57] ABSTRACT

Certain new adducts of benzotriazole and oxazolines are provided in which the oxazolines may contain alkyl, alkenyl or cycloalkyl radicals of from 6 to about 20 carbon atoms. Lubricant compositions are also provided having excellent anticorrosion characteristics when minor amounts of such adducts are added thereto.

14 Claims, No Drawings

OIL-SOLUBLE ADDUCTS OF BENZOTRIAZOLE AND OXAZOLINES AND LUBRICANT COMPOSITIONS CONTAINING SAME

This is a continuation of copending application Ser. No. 785,813, filed Apr. 8, 1977, now abandoned.

BACKGROUND OF THE INVENTION

1. Field of the Invention

This invention relates to a new additive composition containing the reaction product of benzotriazole and a specified oxazoline.

This invention further relates to lubricant compositions which normally cause or induce the oxidative corrosion and/or deterioration of metallic surfaces with which said compositions come in contact. More particularly, in one of its aspects, the invention relates to organic compositions, particularly petroleum derived lubricant compositions, such as mineral lubricating oils, automotive oils, gear oils, heavy circulating oils, transmission fluids, greases, various functional fluids, such as hydraulic fluids, and other forms of organic compositions, such as way lubes, normally requiring the presence of anticorrosion additives and which contain a minor proportion of the aforementioned additive.

2. Description of the Prior Art

Prior to the present invention, benzotriazole has been employed in lubricants as a metal deactivator and as an anticorrosion agent. Benzotriazole-maleic anhydride adducts have also been known and are disclosed in "Elisa Shigi and Franca Rocchi," Gas. Chim. Ital. 84, 183 (1955). It is found, however, that prior art adducts of benzotriazole are not effective anticorrosion agents since they are not generally oil-soluble. High molecular weight bisoxazolines are known and disclosed in German Pat. No. 1,444,904 as antiwear agents.

SUMMARY OF THE INVENTION

In accordance with the present invention, it has been found that anticorrosion properties can be effectively incorporated into lubricant compositions by including an anticorrosion amount of an adduct of benzotriazole and a specified oxazoline. These adducts are soluble in organic compositions, comprising, for example, any of the aforementioned lubrication oils, automotive oils, gear oils, transmission fluids, greases and other forms of lubricating compositions incorporating excellent anticorrosion properties thereto.

It has been found that benzotriazole may be made oil-soluble by reacting it with oxazoline of the structure

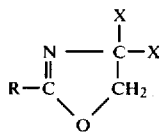

where R is an alkyl, alkenyl, or cycloalkyl radical having from about 6 to about 20 carbon atoms. R can also be derived from a mixture of acids, as for example, monocarboxylic acids, saturated such as oleic or unsaturated such as naphthenic acid. X can by hydrogen, methyl, hydroxymethyl or alkyl of 2 to about 20 carbon atoms. Any suitable carboxylic (monocarboxylic preferably) or fatty acid may be used to derive R. Exemplary are such acids as linoleic, linolenic, benzoic and naphthenic acids. Especially preferred are oleic or a mixture of acids as in naphthenic acids.

The adduct of benzotriazole and the specified oxazolines can be employed in any amount which is effective for imparting the desired degree of anticorrosion properties. In many applications, the adduct is effectively employed in an amount from about 0.001% to about 20%, by weight, and preferably in an amount from about 0.5% to about 5%, by weight, of the total weight of the organic composition.

In general, the benzotriazole and the oxazolines are preferably reacted in a mole ratio of benzotriazole to oxazoline of from about 1:1.5 to about 1:5. This reaction can be conducted at a temperature from about 80° C. to about 200° C. and preferably from about 90° C. to about 110° C. The compositions thus prepared are oil-soluble readily dissolving at 0.1% benzotriazole levels in solvent refined base stock. The additive blends are generally more stable than additive compositions employing benzotriazole alone affording good protection for both steel and copper.

The above-described ester adducts, as previously mentioned, may be incorporated in any lubricating media, which may comprise liquid hydrocarbon or other oils. These oils may be in the form of either a mineral oil or a synthetic oil in the form of a grease in which any of the aforementioned oils are employed as a vehicle. In general, mineral oils, employed as the lubricant, or grease vehicle, may be of any suitable lubricating viscosity range, as, for example, from about 45 SSU at 100° F. to about 6,000 SSU at 100° F., and, preferably, from about 50 to about 250 SSU at 210° F. These oils may have viscosity indexes varying from below zero to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythitol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, and phenoxy phenylethers.

DESCRIPTION OF SPECIFIC EMBODIMENTS

The following examples and comparative data will serve to illustrate the novel adducts of the present invention and the improvement in anticorrosion properties of organic media, and particularly lubricant compositions, containing them.

EXAMPLE 1

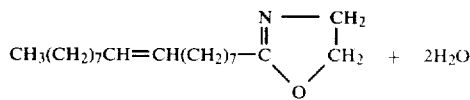

A mixture of oleic acid (56.6 grams, 0.2 mol) and ethanolamine (12.2 grams, 0.2 mol) were heated 24 hours at 200° C. in a stream of nitrogen to carry off water of reaction. At the end of the reaction period, any remaining volatile material was removed from the product by pumping at 0.5 mm Hg and 80° C. for 2 hours. Oxazoline formation was demonstrated by the formation of a new adsorption at 1660 cm$^{-1}$ in the infrared spectrum. The yield of product was 47.7 grams (77%).

In order to prepare the described oxazolinebenzotriazole adducts, a mixture of 3 grams of the oxazoline prepared above and 1 gram of benzotriazole was stirred at 95° C. for 5 minutes. The product was then tested for oil solubility and anticorrosion activity as described below.

EXAMPLES 2–3

The adducts (additives) in these examples were made as in Example 1, however, the relative amounts of benzotriazole and oxazoline were varied as shown below:

| Example | Benzotriazole gms. | Oxazoline of Example 1, gms. |
|---|---|---|
| 2 | 1 | 9 |
| 3 | 1 | 24 |

EXAMPLE 4

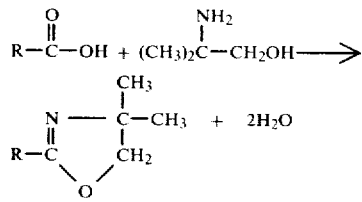

(RCO$_2$H = Naphthenic Acid, equiv. wt. 176.3)

A mixture of naphthenic acid (8.82 g, 0.05 equiv. wt.) and 2-amino-2-methyl-1-propanol (5.34 g. 0.06 mol) was heated at 160° C. for 19 hours with a stream of nitrogen passing through the sample to aid in the removal of water of reaction. The sample was then heated at 135° C. under vacuum (0.5 mm Hg) for 2 hours to remove any remaining volatile impurities. The yield of product was 9.5 grams (83%) of the dimethyloxazoline shown above, as indicated by a strong infrared adsorption at 1660 cm$^{-1}$.

The oxazoline-benzotriazole was prepared as follows: a mixture of 3 grams of the dimethyloxazoline prepared above and 1 gram of benzotriazole was stirred at 95° C. for 5 minutes. The product was then tested for oil solubility and anticorrosion activity as described below.

EXAMPLES 5–6

Different compositions were made as in Example 4, but the relative amounts of benzotriazole and dimethyloxazoline (from Example 4) were varied as shown below:

| Example | Benzotriazole, gms. | Dimethyloxazoline of Example 4, gms. |
|---|---|---|
| 5 | 1 | 9 |
| 6 | 1 | 24 |

Solubility Tests

The additives were tested for solubility in a 150 SUS solvent-refined mineral oil by measuring the time required to dissolve at 65° C., and the time required for formation of haze at 25° C. All additives plus benzotriazole were tested at the 0.1% wt. level. A comparison with unreacted benzotriazole is also shown in Table 1.

TABLE 1

Solubilities of Additives in Lubricating Oils

| Blend (in 150 SUS oil) | Time required to dissolve in oil at 65° C. (minutes) | Time required to form precipitate or haze at 25° C. (hours) |
|---|---|---|
| Example 1 | 11 | 0.4 |
| Example 2 | <1 | 16 |
| Example 3 | <1 | 1 |
| Example 4 | 5 | 0.58 |
| Example 5 | <1 | 42 |
| Example 6 | <1 | 148 |
| Benzotriazole | >240 | <0.5 |

Corrosion Tests

Additives from Examples 2 and 5 where evaluated according to their abilities to protect copper and steel against corrosion by elemental sulfur in oil. The oil blend used for testing was an Arabian Light 150 SUS oil containing 50 ppm of elemental sulfur. The Modified ASLE-64-9 Corrosion Test was used. Copper and steel rods were rated on a scale of 1 (clean) to 10 (completely covered with corrosion).

MODIFIED ASLE-64-9 CORROSION TEST

ASLE SLIDEWAY LUBRICANT ACCELERATED BREAKDOWN TEST

I. Test Procedure for Normal Test Conditions

Place clean polished pieces[1] of copper and carbon steel rods (approximately 0.25 inches diameter by 3.0 inches long) in a 100-cc Griffin beaker containing 35 to 40 grams of oil sample. Put beaker and contents into an electric drying oven for 24 hours, maintaining a temperature of 210°±2° F. (99°±1° C.). Test period may be extended 72 hours, if necessary.

Test results: Condition of Steel Rod; Condition of Copper Rod; Precipitate or Sludge; Evaporation Loss % Wt.

Specimens should be rated "as is" when removed from the oil (no washings); copper and steel rods are rated by comparing them with the attached Mobil Corrosion Standards and assigning the number from 1 to 10 which most closely resembles their condition.

[1] Test specimen pieces must be freshly polished and placed in pentane for >30 minutes before using. These polished specimens must then be used within 30 minutes after the original 30-minutes pentane deactivation period.

TABLE 2

Corrosion Test Results

| Additive | | Metal Specimen Rating | |
|---|---|---|---|
| | | Copper | Steel |
| None | | 9 | 8 |
| Benzotriazole, 0.02% | | 9 | 3 |
| Benzotriazole, 0.04% | | 3 | 1 |
| Example 2, 0.2% total | (0.02% Benzotriazole) (0.18% Oxazoline) | 3 | 2 |
| Example 2, 0.4% total | (0.04% Benzotriazole) (0.36% Oxazoline) | 3 | 1 |
| Example 5, 0.2% total | (0.02% Benzotriazole) (0.18% Dimethyloxazoline) | 3 | 2 |
| Example 5, 0.4% total | (0.04% Benzotriazole) (0.36% Dimethyloxazoline) | 3 | 2 |

The data in the Tables clearly establish the improved oil-solubility and the excellent anticorrosion properties of lubricant compositions employing the novel benzotriazole-oxazoline adducts of this invention.

While this invention has been described with reference to preferred compositions and components therefor, it will be understood by those skilled in the art, that departure from preferred embodiments can be effectively made and are within the scope of the specification.

What is claimed is:

1. Lubricant compositions comprising oils of lubricating viscosity or greases prepared therefrom and containing a minor amount, sufficient to impart anticorrosion properties thereto, of an oil-soluble adduct of benzotriazole and an oxazoline of the structure $$\begin{array}{c} X \\ | \\ N \longrightarrow C-X \\ \parallel \quad\quad | \\ R-C \quad\quad CH_2 \\ \diagdown \,\diagup \\ O \end{array}$$

wherein R is an alkyl, alkenyl or cycloalkyl radical having from about 6 to about 20 carbon atoms, or where R is derived from a suitable carboxylic acid or a mixture of such acids and X is hydrogen, methyl, hydroxymethyl or alkyl of from 2 to about 20 carbon atoms.

2. The composition defined in claim 1 wherein the benzotriazole-oxazoline adduct is present in an amount of from about 0.001% to about 20%, by weight.

3. The composition defined in claim 1 wherein the adduct is present in an amount of from about 0.5% to about 5%, by weight.

4. The composition defined in claim 1 wherein said composition comprises an oil of lubricating viscosity.

5. The composition defined in claim 4 wherein said oil of lubricating viscosity is a mineral oil.

6. The composition defined in claim 1 wherein said composition comprises a grease.

7. The composition defined in claim 1 wherein R is derived from oleic acid and X is hydrogen.

8. The composition defined in claim 1 wherein R is derived from naphthenic acid and X is methyl.

9. A compound constituting the adduct of benzotriazole and an oxazoline of the structure $$\begin{array}{c} X \\ | \\ N \longrightarrow C-X \\ \parallel \quad\quad | \\ R-C \quad\quad CH_2 \\ \diagdown \,\diagup \\ O \end{array}$$

where R is an alkyl, alkenyl or cycloalkyl radical having from about 6 to about 20 carbon atoms or where R is derived from a suitable carboxylic acid or mixture of such acids and X is H, $CH_3$, $CH_2OH$ or alkyl of from 2 to about 20 carbon atoms.

10. The adduct of claim 9 wherein R is derived from oleic acid and X is H.

11. The adduct of claim 9 wherein R is derived from naphthenic acid and X is $CH_3$.

12. A method for preparing the compound of claim 9 which comprises reacting benzotriazole and said oxazoline at a temperature of 80°-200° C. in a mole ratio of benzotriazole to oxazoline of about 1:1.5 to about 1:5.

13. The method of claim 12 wherein R of said oxazoline is derived from oleic acid and X is H.

14. The method of claim 9 wherein R of said oxazoline is derived from naphthenic acid and X is $CH_3$.

* * * * *